(12) United States Patent
Jørgensen et al.

(10) Patent No.: US 7,154,600 B2
(45) Date of Patent: Dec. 26, 2006

(54) AUTOMATIC PARTICLE ANALYZING SYSTEM

(75) Inventors: Terje Jørgensen, Skien (NO); Frode Reinholt, Skien (NO); Ole Magne Johnsen, Skien (NO)

(73) Assignee: Norsk Hydro ASA, Oslo (NO)

( * ) Notice: Subject to any disclaimer, the term of this patent is extended or adjusted under 35 U.S.C. 154(b) by 262 days.

(21) Appl. No.: 10/476,790

(22) PCT Filed: May 7, 2001

(86) PCT No.: PCT/NO01/00191

§ 371 (c)(1),
(2), (4) Date: May 14, 2004

(87) PCT Pub. No.: WO02/090942

PCT Pub. Date: Nov. 14, 2002

(65) Prior Publication Data

US 2004/0233430 A1    Nov. 25, 2004

(51) Int. Cl.
*G01N 15/02*    (2006.01)
(52) U.S. Cl. .................. 356/335; 356/337; 356/336
(58) Field of Classification Search ........ 356/337–343, 356/336, 335; 250/222.2
See application file for complete search history.

(56) References Cited

U.S. PATENT DOCUMENTS

| | | | | |
|---|---|---|---|---|
| 5,011,285 A | * | 4/1991 | Jorgensen et al. | .......... 356/335 |
| 5,309,215 A | | 5/1994 | Schumann | |
| 5,309,773 A | * | 5/1994 | Tokoyama | ............... 73/863.01 |
| 2003/0156285 A1 | * | 8/2003 | Johnsen et al. | ............. 356/335 |

FOREIGN PATENT DOCUMENTS

| | | |
|---|---|---|
| EP | 0 252 407 | 1/1988 |
| JP | 62-175645 | 8/1987 |
| WO | 01/84115 | 11/2001 |

* cited by examiner

*Primary Examiner*—Layla G. Lauchman
*Assistant Examiner*—Tri Ton
(74) *Attorney, Agent, or Firm*—Wenderoth, Lind & Ponack, L.L.P.

(57) ABSTRACT

A method and an apparatus for automatic analysis of particle size distribution, shape and color. The method includes collection of a particle sample, where the particles are distributed into a substantially monolayer particle curtain to be exposed to a light source for providing imaging and subsequent analysis of the particles. The apparatus has a sampling device that collects samples from the product stream integrated in the system.

15 Claims, 4 Drawing Sheets

AUTOMATIC PARTICLE ANALYZING SYSTEM

BACKGROUND OF THE INVENTION

1. Technical Field of the Invention

The present invention relates to a method and an apparatus for automatic sampling and for performing an automatic image analysis to determine a particle size distribution, shape characterization and shape distribution.

2. Description of Related Art

It is important for example in the fertilizer industry to have reliable information about the end product size distribution and particle shape, as optimal values for these parameters are of importance both from a purely economical point of view and when using the product, e.g. when spreading the produced prills or granules. Furthermore, a process will be most economical if it gives a product with a narrow sieve span, without having to sieve away large fractions that have to be run in return.

A method and apparatus for this use is known from U.S. Pat. No. 5,011,285. The method includes the collection of particle samples and the generation of a particle curtain in a monolayer form. The particle curtain is formed by taking particles through a silo down onto a vibrating plate. The particle curtain is lit up and the images of the particles therein is recorded and analyzed. The silo has at least one level sensor to record the level of particles in the silo and to give a signal to the sampler.

In U.S. Pat. No. 5,309,215 there is also shown an apparatus for the determination of particle size distribution based on the same principle. Particles are fed from a sample collection chamber to a conveyor band or vibrating channel forming a particle curtain when falling down from this band or channel.

Both of these methods are dependent on a separate collection of the samples. The samplers commonly used in such processes are conveyor belt samplers comprising for example a container with a longitudinal slit that passes across the product stream on the conveyor belt or collects the samples at the end of the conveyor belt in such a way that the particles can fall gravimetrically into the sampler when it traverses the product stream. Also in production pipes, samplers collect particles from a cross section of the product stream.

The samples thereafter have to be transferred to the container/sample collection chamber before they can be analyzed. To install such a sampling and analyzing system often involves comprehensive reconstruction of the production line to fit a sampling system, if at all possible. For example by installation of an end of a conveyor belt sampler, the end of conveyor belt housing (covering) has to be reconstructed to fit the sampling system. The expense of such a comprehensive reconstruction of the process line can be a reason not to invest in an imaging analysis equipment. For some installations it could also be very difficult to find space in the process line for a sampling system or to find a sampling system that could be used in an existing process.

SUMMARY OF THE INVENTION

The object of the invention is to obtain a simple, sturdy and cheap particle analyzing that easily can be used in existing production facilities without extra investment and reconstruction. Another object is to arrive at a versatile and automatic method and apparatus for analysis of a plurality of samples applicable for on-line analysis.

These and other objects of the invention are obtained with the method and apparatus as described below, and the invention is further defined and characterized by the accompanying patent claims.

The invention thus concerns an automatic particle analyzing system and a method for automatical analysis of particle size distribution, shape and color. The analyzing system comprises sampling means and a device for creating a particle mono curtain suitable for imaging and subsequent analysis, wherein a sampling device is an integrated part of the system. The sampling device could be a tube moveable from a lower sampling position to an upright position where the sample is transferred directly onto a vibrating plate/trough for creating a particle curtain. Alternatively, the sampling device is a plate/trough that is vertically movable from a lower sampling position to an upper position where it is used to create a particle curtain. The plate/trough could be rectangular with an end wall and parallel sidewalls or be a plate with non-parallel sidewalls. The sampling device, device for distributing the sample into a mono curtain, light source and recording means are all mounted to a frame that could be fixed to a conveyor belt.

The integrated sampling device collects samples directly from the product stream. It is preferred to collect a vertical cross section of the product stream and do the sampling counter current to the product stream. It is preferred to use a sampling tube which is vertically movable from a lower sampling position to an upright position where the sample is fed directly to a vibrating plate for creating a particle curtain. Alternatively, the sample is collected by lowering the vibrating plate/trough into the product stream and thereafter lifting the plate to an upper position where the plate is vibrated to create a particle curtain. A new sample is automatically collected when the last particle on the plate is analyzed.

BRIEF DESCRIPTION OF THE DRAWINGS

The invention will now be further explained in the following embodiments with reference to the accompanying drawings, FIGS. 1–4, wherein.

Figure 1A:
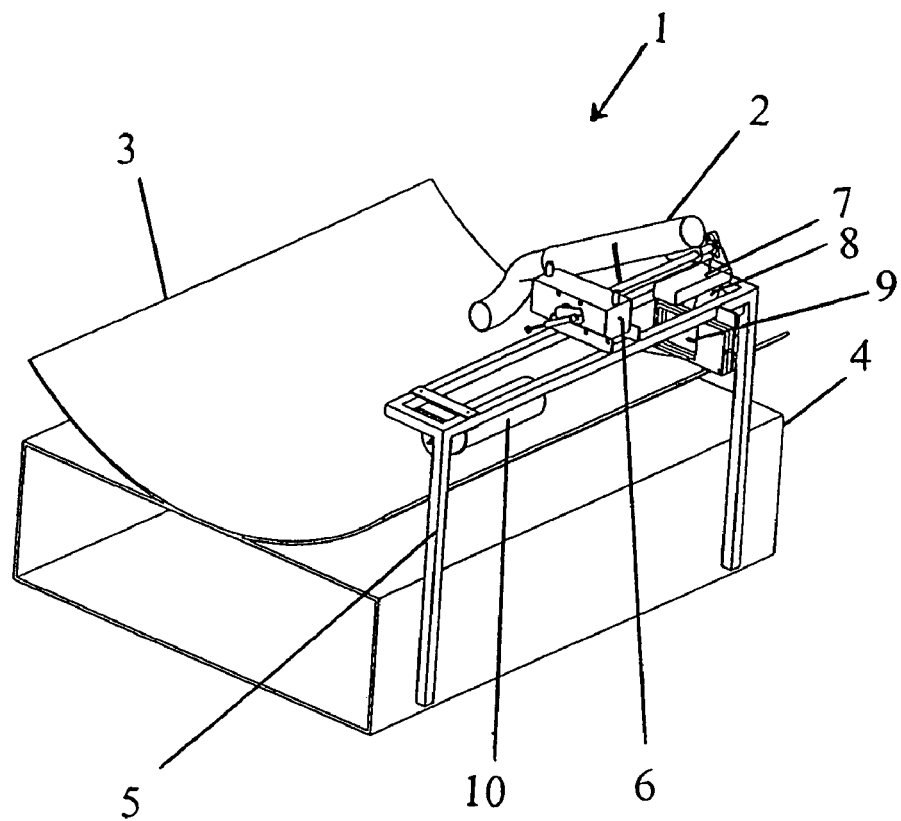
FIG. 1A is a perspective view of a particle analyzer with the sampler tube in a lower sampling position.
Figure 1B:
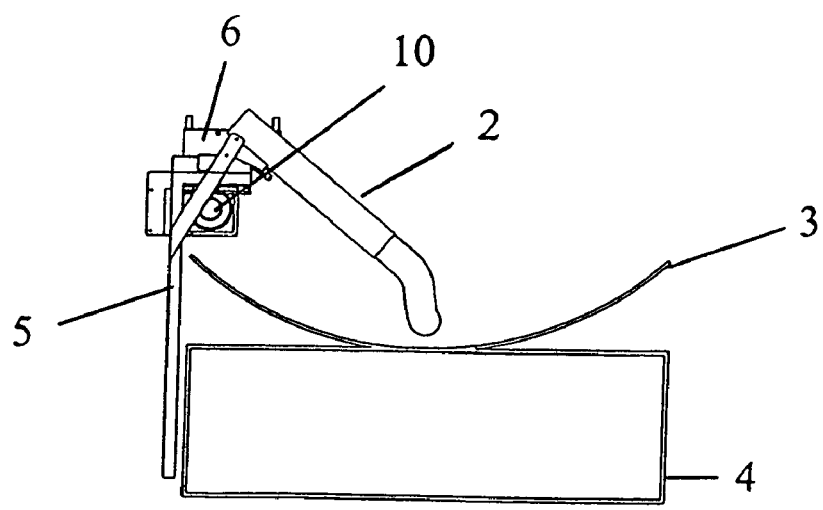
FIG. 1B is a side view of the sampler in a lower sampling position.
Figure 2:
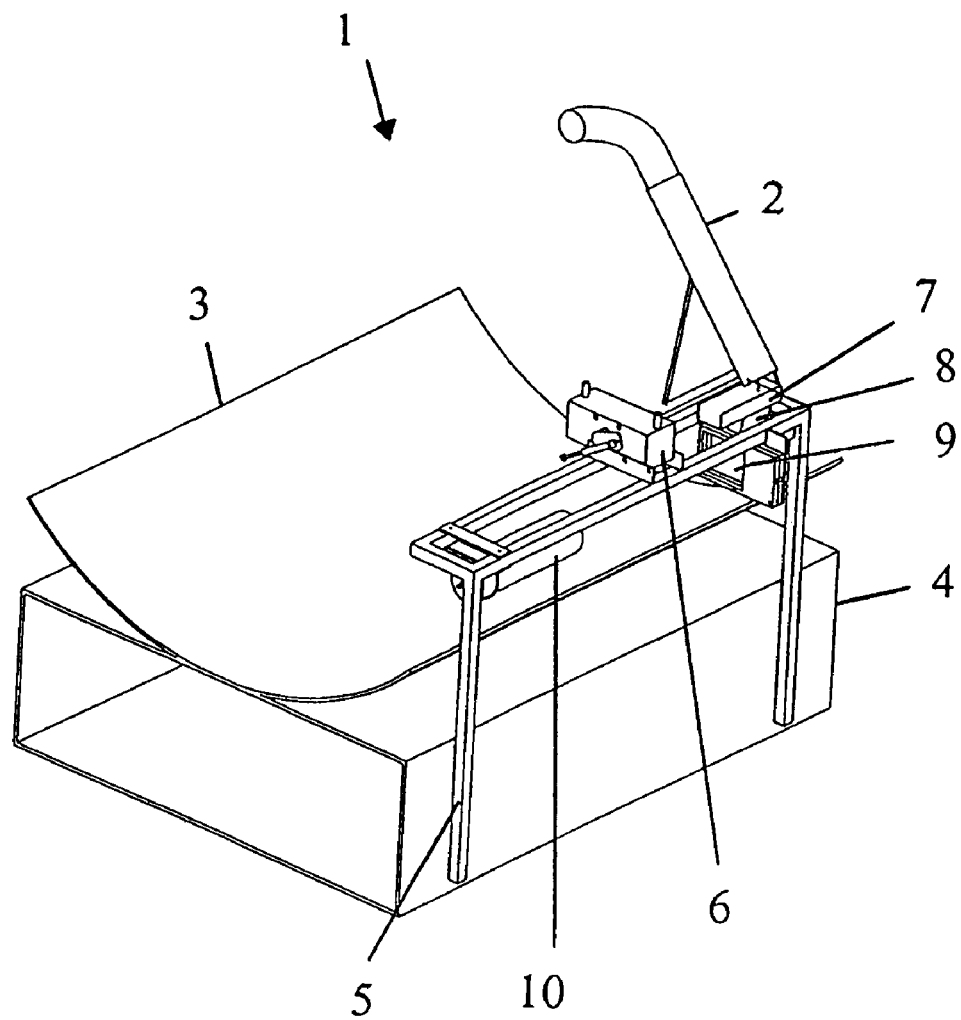
FIG. 2 is a perspective view with the sampler tube in an upper position (emptying sample to the vibrating system)

A particle analyzer 1 is shown in FIGS. 1A, 1B and 2, and includes a sampler 2 for collecting particle samples in a process, for example at a conveyor belt 3 as shown in the figures. The conveyor belt is mounted upon a frame 4. The sampler 2 is shown as a tube with a bent lower part. The sampler is fixed to a mounting frame 5 so as to be vertically movable. The frame has two vertically extending legs adapted to be fixed to the conveyor belt frame 4, and an upper horizontal part, to which the other components of the analyzer are fixed. A pneumatic cylinder 6 is used to drive the sampler between an upper position and a lower position.

In FIGS. 1A and 1B the sampling tube is shown in its lower sampling position collecting samples into one end of the tube in the product stream on the conveyor belt, while FIG. 2 illustrates the sampler in an upright position where the collected sample falls from the sample collected end of the tube onto a plate 7 or trough. The plate 7 is mounted to a vibrator 8 which may vibrate in a known manner, and both the frequency and the amplitude may be regulated. In these figures the vibrator 8 is shown mounted below the plate 7. By vibrating the plate the particles will run out over its edge creating a particle curtain. By adjusting the vibration amplitude and/or frequency, one can easily make sure that the particles fall down from the plate into a substantially monolayer of particles. This is controlled by a computer and thus overlapping particles in the image is avoided.

The sampler could be of different design. It could be in the form of a straight or bent pipe. A pipe with a rectangular cross section is also possible to use. What is most important is that it has a shape that makes it possible to collect samples in the product stream. It is also important that the diameter of a pipe sampler is at least 2–3 times the diameter of the product to be analyzed, to make sure that there is a free flow of the product.

A light source 9 is mounted to the frame 5 below the vibrating plate 7. The particle stream or particle curtain is thus lit up by the light source. The light source could be a normal lamp, a set of laser beams or a flash which lights at a signal. A unit 10 mounted at the other side of the frame may be a film or video camera, but also a recording unit for penetrating light, for example laser beams. The particle stream from the vibrating plate thus falls between the light source and camera 10. A video camera that takes images all the time is preferably used, but if the light source is a flash the images will be recorded only at each flash. Pictures are obtained by using a video camera to take pictures of the monolayer of particles. Thereby both the shape and size distribution can be registered. Special computer programs for the calculation of shape characterization or the deviation from the desired shape are used and the particle size distribution in the product stream determined. Generation of the particle curtain and analyzing the particles can be carried out continuously, and the production parameters can be adjusted as a function of the result of the analysis.

The vibrating plate or trough, is shown in FIGS. 1A, 1B and 2 as a rectangular plate with one end wall and two parallel sidewalls. This shape is especially used for coarse particles. For smaller particle products, a vibrating plate with sidewalls that are not parallel can be used, giving a narrower passage for the particles before they fall over the edge forming a particle curtain. When imaging small particle products, the camera 10 must be located closer to the product and it is therefore not necessary with a very wide particle curtain. The computer will regulate the number of particles. The passage out from the trough should at least be 2–3 times the largest diameter of the particles. However, if wanted, it is possible to mount more than one camera to cover a wider particle area or different camera selection for different particle ranges. The shape of the trough that is selected, will be dependent on the product to be analyzed.

Figure 3A:
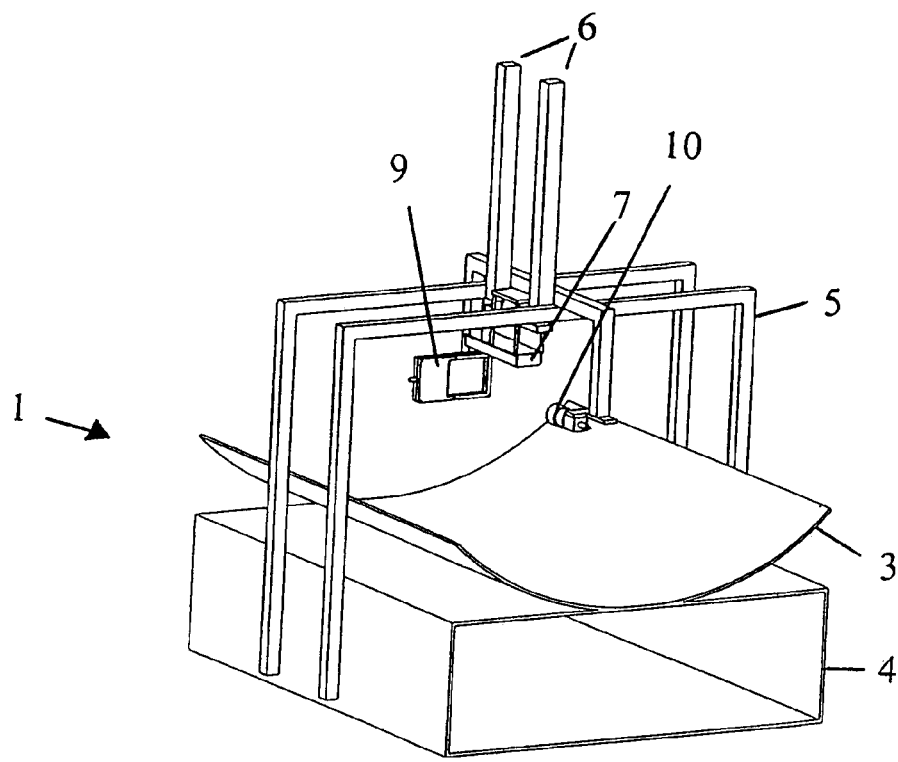
FIG. 3A is a perspective view of an alternative configuration of the particle analyzer with the sampler in an upper position.
Figure 3B:
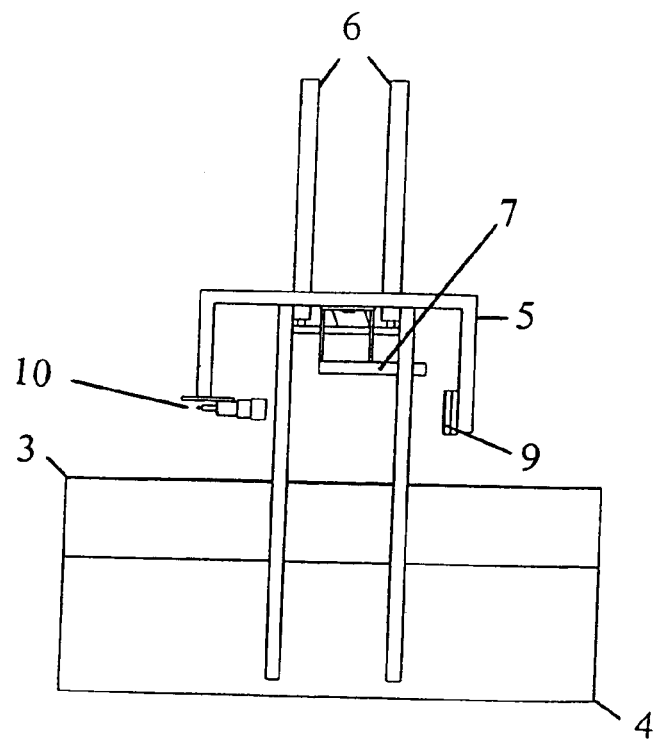
FIG. 3B is a side view of the analyzer with vibrating plate sampler in an upper position.
Figure 4A:
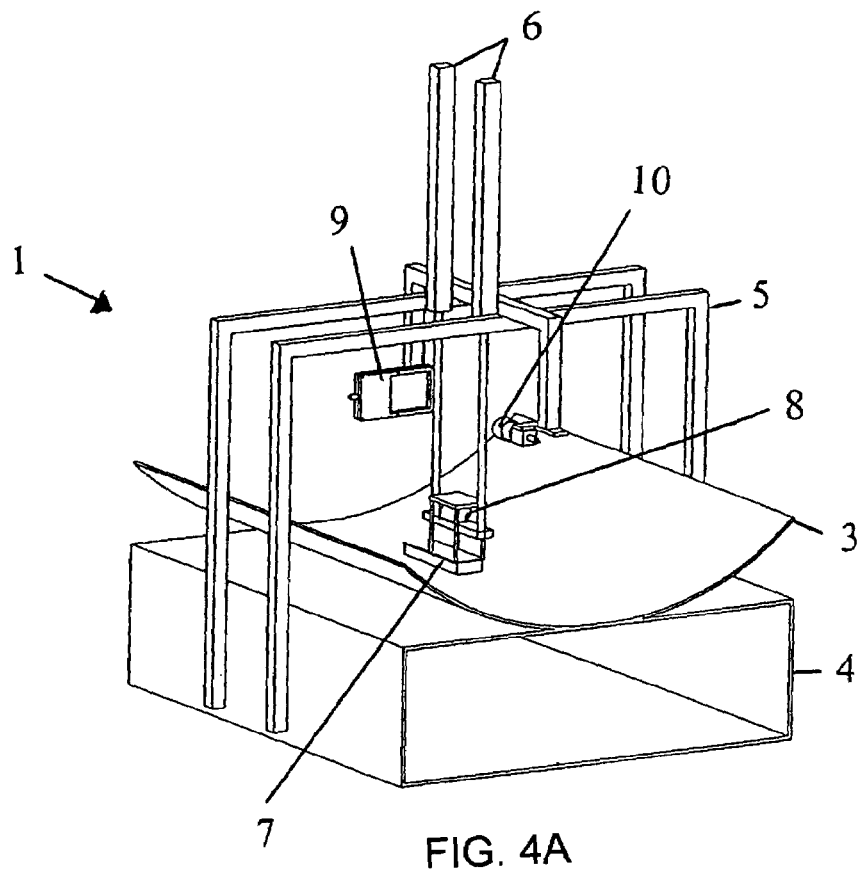
FIG. 4A is a perspective view of the alternative configuration of the particle analyzer with the sampler in a sampling position.
Figure 4B:
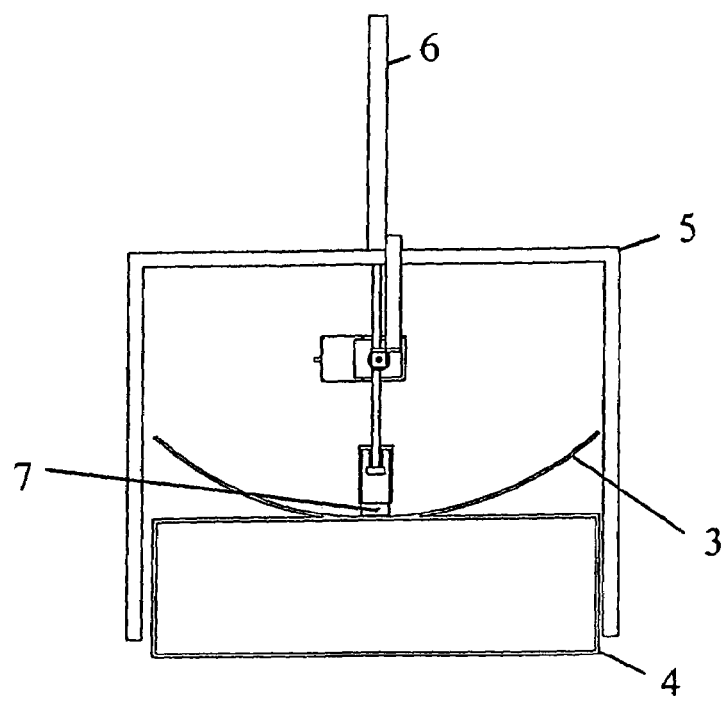
FIG. 4B is a side view of the analyzer with the vibrating plate sampler in a lower position.

Instead of using a sampling device as illustrated in FIGS. 1A, 1B and 2, it is also possible to use the vibrating trough to collect the samples. An alternative particle analyzer is illustrated in FIGS. 3A, 3B, 4A and 4B. The vibrating trough 7 is shown mounted below the vibrator 8 to a frame 5 (FIG. 4A). This frame has an upper horizontal part and four vertical legs mounted on opposite sides of the conveyor frame 4. Pneumatic cylinders 6 fixed to the frame 5, lower the trough 7 down into the product stream on the conveyor belt 3 as illustrated in FIGS. 4A and 4B. A sample is collected and the trough is lifted to the upper position as illustrated in FIGS. 3A and 3B. Thereafter the vibrator is activated and a particle curtain is formed, imaged by using flash 9 and camera 10, recorded and analyzed. When the trough is empty, a new sample is collected.

When using the apparatus according to the invention, sampling is carried out counter current to the product stream on the conveyor belt. The sampler is lowered into the product stream. A vertical cross section of the product is collected and this will be close to an average particle distribution. This will result in samples that are representative enough to control a production process.

Each time all the particles in the sample are analyzed, the sampler will move to the product stream again to collect a new sample. The analyzed sample falls directly down onto the conveyor belt again. In this way analysis and sampling is repeated continuously. However, it is also possible to control the sampling frequency in other ways. Often it could be sufficient just to analyze a certain number of particles in a sample. The vibrating plate will be emptied of particles before a new sample is taken. It is also possible to take product samples at set intervals.

The mounting frame 5 should be fixed to the frame 4 of a conveyor. It could be mounted on the one side of the conveyor belt as illustrated in FIGS. 1A, 1B and 2 or across the conveyor belt as illustrated in FIGS. 3A, 3B, 4A and 4B. It is preferred to mount the frame in the longitudinal direction. This makes it easier to adjust the camera when this is necessary.

The method and the apparatus according to the invention may be applied to all known particulating processes and processes where the addition of particles with the desired size distribution and shape is important. The invention could be used to analyze all kinds of dry particles, apart from fertilizer, for example broken stone, sand, products in the food industry etc. The invention will, however, be applicable for verification of finished particulate product too. Such application may be: analysis during bulk loading, packing in bags or the like or verification of the specification of particulate products. The invention could be used both for conveyor belt or pipeline installations.

The invention claimed is:

1. An automatic particle analyzing system comprising:
a sampling device; and
a device for creating a particle curtain in a monolayer form suitable for imaging and subsequent analysis, wherein the sampling device is an integrated part of the system,
wherein the sampling device is a tube that is moveable from a lower sampling position to an upright position where the sample can be transferred directly onto a vibrating plate or trough for creating a particle curtain.

2. The automatic particle analyzing system according to claim 1, wherein the plate or trough is rectangular with an end wall and parallel side walls.

3. The automatic particle analyzing system according to claim 1, wherein the plate or trough has non-parallel side walls.

4. An automatic particle analyzing system comprising:
a sampling device; and
a device for creating a particle curtain in a monolayer form suitable for imaging and subsequent analysis, wherein the sampling device is an integrated part of the system, wherein the sampling device is a plate or trough that is vertically movable from a lower sampling position to an upper position where it can be used for creating a particle curtain.

5. The automatic particle analyzing system according to claim 4, wherein the plate or trough is rectangular with an end wall and parallel side walls.

6. The automatic particle analyzing system according to claim 4, wherein the plate or trough has non-parallel side walls.

7. An automatic particle analyzing system comprising:
a frame adapted to be fixed to a conveyor frame;
a sampling device mounted on the frame, wherein the sampling device is an integrated part of the system; and
a device for creating a particle curtain in a monolayer form suitable for imaging and subsequent analysis;
a light source; and
a recording unit,
wherein the sampling device, the device for creating a particle curtain, the light source and the recording unit are mounted to the frame.

8. The automatic particle analyzing system according to claim 7, wherein the frame is adapted to be mounted across a conveyor belt or along one side thereof.

9. A method for automatic analysis of particle size distribution, shape and color, the method comprising:
collecting a particle sample from a product stream with a sampling device; and
distributing the particles substantially into a particle curtain in a monolayer form that is to be exposed to a light source for providing imaging and subsequent analysis of the particles,
wherein the sampling device that collects samples from the product stream is integrated in the system, and
wherein the sampling device is a sampling tube, and the sampling tube is movable from a lower sampling position to an upright position where the sample is fed directly to a vibrating plate for creating the particle curtain.

10. The method according to claim 9, wherein a vertical cross section of the product stream is collected.

11. The method according to claim 9, wherein sampling is carried out countercurrent to the product stream.

12. A method for automatic analysis of particle size distribution, shape and color, the method comprising:
collecting a particle sample from a product stream; and
distributing the particles substantially into a particle curtain in a monolayer form that is to be exposed to a light source for providing imaging and subsequent analysis of the particles,
wherein the sampling device that collects samples from the product stream is integrated in the system, and
wherein the particle sample is collected by lowering a plate or trough into the product stream and thereafter lifting the plate or trough to an upper position where the plate is vibrated to create the particle curtain.

13. The method according to claim 12, further comprising automatically collecting a new sample when the last particle on the plate is analyzed.

14. The method according to claim 12, wherein a vertical cross section of the product stream is collected.

15. The method according to claim 12, wherein sampling is carried out countercurrent to the product stream.

* * * * *